United States Patent [19]

Drewlow

[11] Patent Number: Plant 6,002

[45] Date of Patent: Sep. 1, 1987

[54] IMPATIENS PLANT NAMED CIRRUS

[75] Inventor: Lyndon W. Drewlow, Ashtabula, Ohio

[73] Assignee: Mikkelsens, Inc., Ashtabula, Ohio

[21] Appl. No.: 786,073

[22] Filed: Oct. 10, 1985

[51] Int. Cl.[4] ..... A01H 5/00
[52] U.S. Cl. ..... Plt./68
[58] Field of Search ..... Plt./68

*Primary Examiner*—James R. Feyrer

*Attorney, Agent, or Firm*—Schwartz, Jeffery, Schwaab, Mack, Blumenthal & Evans

[57] ABSTRACT

An Impatiens plant named Nova particularly characterized as to uniqueness by the combined characteristics of relatively early flowering, white flowers with five petals in which the upper petal has a green blotch showing through; vigorous and highly self-branching growth habit; green stems carrying relatively long and broad green leaves having uniform greenish yellow variegation; excellent flower keeping qualities, and ideal suitability for hanging baskets.

1 Drawing Figure

The present invention relates to a new and distinct cultivar of Impatiens plant, botanically known as Impatiens, named Cirrus. Cirrus was developed by me in Ashtabula, Ohio through controlled breeding by crossing Mikkelsen Seedling No. 83-326-2 (seed parent) with Mikkelsen Seedling No. 83-307-1 (pollen parent), both of which are unpatented.

Asexual reproduction by terminal or stem cuttings taken by me in Ashtabula, Ohio has shown that the unique features of this new Impatiens are stabilized and are reproduced true to type in successive propagations.

The following characteristics distinguish Cirrus from both its parent cultivars and other cultivated Impatiens of this type known and used in the floriculture industry:

1. Cirrus is 7 to 10 days earlier to bloom than Milkyway, (disclosed in U.S. Plant Pat. No. 5,125), which is in turn similar in many respects to 83-326-2, the female parent of Cirrus.

2. The flowers of Milkyway and Cirrus are white and similar in size and do not pink during normal summer temperatures. However, Cirrus has more flowers early in the blooming period and blooms better under low light conditions. Further, the upper petal of Cirrus has a green blotch on the underside of the petal which is visible on the upper surface of the petal. The upper petal of Milkyway has only a very small green blotch on its under surface, with the blotch being surrounded by a red area and not being visible on the upper surface.

3. The vigorous growth habit of Cirrus makes it ideal for hanging basket and large pot production. Overall plant size is similar to Corona (disclosed in U.S. Plant Pat. No. 5,184).

4. Cirrus has green stems while Milkyway has reddish stems under outdoor growing conditions.

5. The leaves of Cirrus are longer and broader than Milkyway, and are not glossy.

6. Cirrus has very regular variegation while Milkyway can have variable variegation ranging from no variegation to heavy variegation.

7. Cirrus is highly self-branched, and cutting production is above normal, thereby making propagation easy.

8. Cirrus has demonstrated tolerance to low temperature, with plants performing well from a May 15 planting when temperatures were still in the 40° F. to 50° F. range.

9. Flowers have excellent keeping qualities and are carried above the foliage making the plant very colorful.

10. An excellent cultivar for further hybridizing for hanging basket use.

The accompanying colored photograph illustrates the overall appearance of this cultivar in perspective view and shows the colors as true as it is reasonably possible to obtain in a colored reproduction of this type.

The following is a detailed description of my new Impatiens cultivar based on plants produced under commercial practices in Ashtabula, Ohio. The photograph was taken in September of plants grown in a greenhouse. Color references are made to The Royal Horticultural Society Colour Chart except where general terms of ordinary dictionary significance are used.

Parentage: Controlled cross of Mikkelsen Seedling 83-326-2×Mikkelsen Seedling 83-307-1.

Propagation:

(A) *Type cutting.*—15 mm long will develop to 4–5 cm long in 18–21 days.

(B) *Time to root.*—8–10 days at 23° C. summer; 10–12 days at 20° C. winter.

(C) *Rooting habit.*—Heavy, fibrous.

Plant description:

(A) *Form.*—Symmetrically mounded, self-branching, vigorous growing flowering herb; light green stems.

(B) *Habit of growth.*—Continuous flowering, self-branching, mounded, semi-tall, and vigorous, making it ideal for hanging baskets.

(C) *Foliage.*—Broad, non-glossy dark green foliage with greenish yellow variegation extending approximately two thirds of the way up the leaf. (1) Size: 9 to 10 cm long and 3 to 3.5 cm wide on mature leaves. (2) Shape: Lanceolate with acuminate apex and acute base. (3) Texture: Upper side augose, glabrous underside. (4) Margin: Finely serrated, very finely ciliated. (5) Color: Young foliage top side, 137B. Young foliage under side, 138A. Mature foliage top side, 147A. Mature foliage under side, 147B. (6) Veination: Pinnate.

Flowering description:

(A) *Flowering habits.*—Flowers continuously from leaf whorl in progressive and orderly manner with one flower per axil. It takes 5 to 7 days from bud to bloom, and flowers last 2 to 3 weeks.

(B) *Natural flowering season.*—Indeterminant and continuous. Quantity of flowering increases with increasing levels of light.

(C) *Flower buds.*—Ellipsoidal, flowers perfect; whitish green spur up to 3 cm long on mature bud with throat behind ovary and originating from major sepal.

(D) *Flowers born.*—On individual short pedicels from whorl of usually five leaves, flowering progressively around the whorl as leaves and buds develop; flowers are carried above leaf canopy.

(E) *Quantity of flowers.*—Very floriferous; flowering development is continuous so that tight buds to mature blooms simultaneously appear.

(F) *Petals.*—(1) Shape: Heart shaped; top and two bottom petals approximately the same size; two side petals smaller. (2) Color top side when opening: 155A, with blush of 143D on upper petal; similar on both young and mature flowers; under side 155A with a 143C blotch on back of upper petal. (3) Number of petals: Five. (4) Size of flowers: 4.5 to 5 cm in diameter.

(G) *Reproductive organs.*—(1) Stamens: Five in number. (a) Anther shape: Hooded, greenish white in color. (b) Pollen color: Cream. (2) Pistils: Five. (a) Stigma shape: Segmented, column shaped; greenish white in color. (b) Style color: Clear. (c) Ovaries: Five in number, celled, size 4 mm until fertilized; green in color.

Disease resistance: No significant disease or insect problems noted to date.

I claim:

1. A new and distinct cultivar of Impatiens named Cirrus, as described and illustrated, and particularly characterized by the combined features of relatively early flowering, white flowers with five petals in which the upper petal has a green blotch showing through; vigorous and highly self-branching growth habit; green stems carrying relatively long and broad green leaves having uniform greenish yellow variegation; excellent flower keeping qualities, and ideal suitability for hanging baskets.

* * * * *

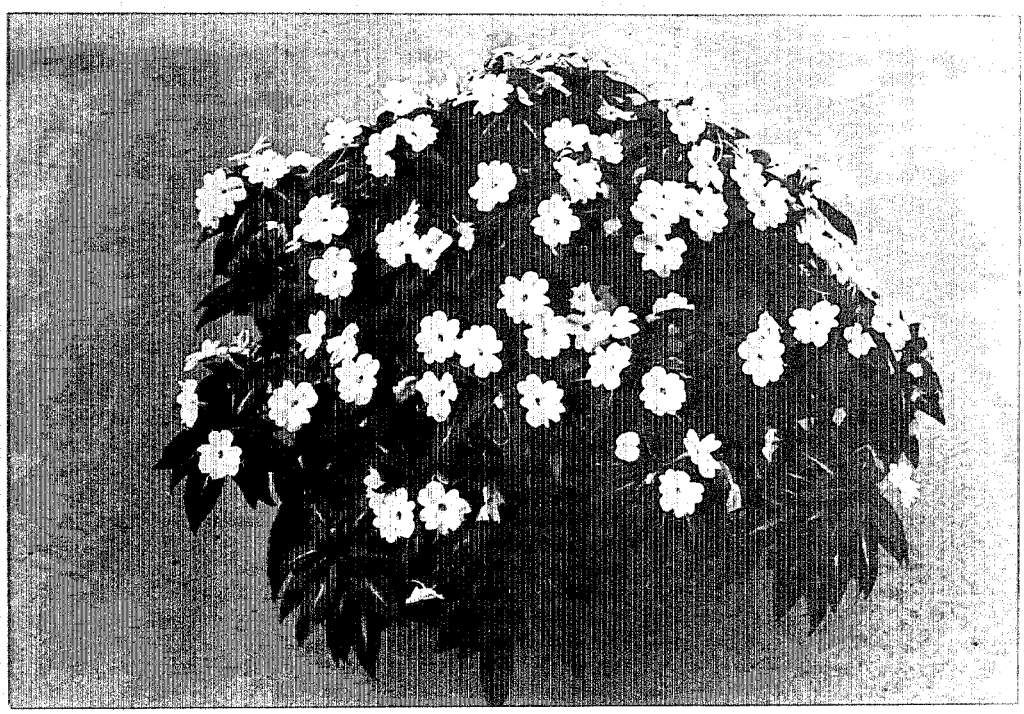

UNITED STATES PATENT AND TRADEMARK OFFICE

CERTIFICATE OF CORRECTION

PATENT NO. : Plant 6,002

DATED : Sep. 1, 1987

INVENTOR(S) : Lyndon W. Drewlow

It is certified that error appears in the above-identified patent and that said Letters Patent is hereby corrected as shown below: On the Title Page:

Item [57], line 1, change "Nova" to --Cirrus--

Signed and Sealed this

Twenty-third Day of February, 1988

*Attest:*

DONALD J. QUIGG

*Attesting Officer*

*Commissioner of Patents and Trademarks*